United States Patent [19]

Meier et al.

[11] Patent Number: 6,079,412
[45] Date of Patent: Jun. 27, 2000

[54] PROCESS AND DEVICE FOR CONTROLLING AND ASSISTING NATURAL BREATHING AND MECHANICAL RESPIRATION

[76] Inventors: Bernd Horst Meier, Clemensstr. 4, D-64285 Darmstadt; Helmut Otto Heinemann, Am Hohenstein 25, D-65779 Kelkheim, both of Germany

[21] Appl. No.: 09/061,229

[22] Filed: Apr. 16, 1998

[30] Foreign Application Priority Data

Apr. 18, 1997 [DE] Germany .......................... 197 16 166

[51] Int. Cl.[7] .................................................. A61M 16/00
[52] U.S. Cl. .............................. 128/204.23; 128/204.18; 600/529; 600/547
[58] Field of Search ...................... 128/204.29, 204.26, 128/202.22, 204.18, 204.23; 600/529, 547; 607/4

[56] References Cited

U.S. PATENT DOCUMENTS

| | | | |
|---|---|---|---|
| Re. 30,101 | 9/1979 | Kubicek et al. ........................ | 600/547 |
| 3,923,055 | 12/1975 | Hammacher . | |
| 4,289,142 | 9/1981 | Kearns .................................... | 600/529 |
| 4,898,176 | 2/1990 | Petre . | |
| 4,951,682 | 8/1990 | Petre . | |
| 5,000,190 | 3/1991 | Petre . | |
| 5,178,151 | 1/1993 | Sackner .................................. | 600/485 |
| 5,197,467 | 3/1993 | Steinhaus et al. ...................... | 600/547 |
| 5,203,337 | 4/1993 | Feldman . | |
| 5,375,604 | 12/1994 | Kelly et al. ............................. | 600/484 |
| 5,766,208 | 6/1998 | McEwan ................................. | 600/595 |

FOREIGN PATENT DOCUMENTS

| | | |
|---|---|---|
| 26 20 285 | 9/1977 | Germany . |
| WO 89/12421 | 12/1989 | WIPO . |
| WO 92/19157 | 11/1992 | WIPO . |

*Primary Examiner*—John G. Weiss
*Assistant Examiner*—V. Srivastava
*Attorney, Agent, or Firm*—Birch, Stewart, Kolasch & Birch, LLP

[57] ABSTRACT

Procedure of mechanical support of natural respiration and process of an artificial respiration with simultaneous registration of mechanical cardiac action via measurement of electric impedance variations within the region of the throat, breast and/or epigastrum, wherein a course of application of respiratory gas supply and respiratory gas restore carried out by the respiratory apparatus is controlled by progress of a measured impedance curve.

9 Claims, 1 Drawing Sheet

PROCESS AND DEVICE FOR CONTROLLING AND ASSISTING NATURAL BREATHING AND MECHANICAL RESPIRATION

BACKGROUND OF THE INVENTION

The invention refers to a procedure and device for the assistance of natural spontaneous respiration as well as implementation of mechanical ventilation by recording electrical impedance in the area of the neck and chest, which is influenced by heart action and blood circulation, as well as for controlling a respirator with information derived from electrical impedance measurements.

The assistance of natural spontaneous respiration and substitution of natural spontaneous respiration by respirators is an important factor for resistance and efficiency of an organism under extreme conditions i.e. altitude physiology, deep sea diving medicine, aviation and space medicine. Artificial ventilation (i.e. mechanical ventilation) assists and replaces functions of spontaneous respiration and guarantees a vital oxygen demand of organs and transportation of metabolic carbon dioxide.

In a natural inspiring organism a negative thoracic pressure is produced by movements of the diaphragm and ribs, the consequence of which breathed air flows into the lungs. In artificial ventilation, inspired air is moved from the outside into the lungs by a higher pressure during an inspiration period. In assisted ventilation the pressure difference generated by the movements of the ribs and diaphragm—negative pressure in the thorax cavity—is reinforced by a higher outward pressure built up by a respirator.

The assistance of natural breathing by respirators requires a sophisticated control of the respirators, whereas a quality of this type of ventilation depends essentially on adaptation of a respirator control system to spontaneous breathing intended by the ventilated person. Mechanical ventilation using an intermittent positive pressure (intermittent positive pressure ventilation IPPV) during inspiration period changes the pressure and circulation conditions which are present in spontaneous breathing persons. Versprille et al. shows, that in mechanical ventilation, cardiac output decreases significantly during the insufflation of breathing volume. In the same way pulmonary perfusion and the veneous return via the upper and lower vena cava is afflicted by the pressure changes in the thoracic cavity.

From the impedance curves, measurable in the area of the chest, information concerning cardiac output, ejection and filling time of the heart, valve function, myocardial work, and the thoracic blood, air and fluid content can be derived depending on the placement of current and measuring electrodes.

SUMMARY

The invention uses impedance changes measurable in the chest area for control of mechanical ventilation. Under control of the mechanical ventilation, all processes are summarized, which might cause a change in the application of respiration pressure, the composition of respirator gas, the temperature and the electrical charge of the respirator gas during inspiration and exspiration.

The use of impedance cardiography for ventilation control offers, in contrast to, the use of other measuring signals the advantage that volume shifts caused by heart action and respiration might be directly recorded without any noticeable latency.

The use of the arterial pressure curve for the control of respiration, i.e. by cannulating the radial arteria, is afflicted with a latency of the mechanical impedance and pulse wave transfer time between heart and pressure transducer.

If electrocardiography were to be appropriately used for the control of respiration, the latency between electrical and mechanical heart action would remain widely unnoticed for the control of the respirator.

DESCRIPTION OF THE PREFERRED EMBODIMENT

Figure 1:
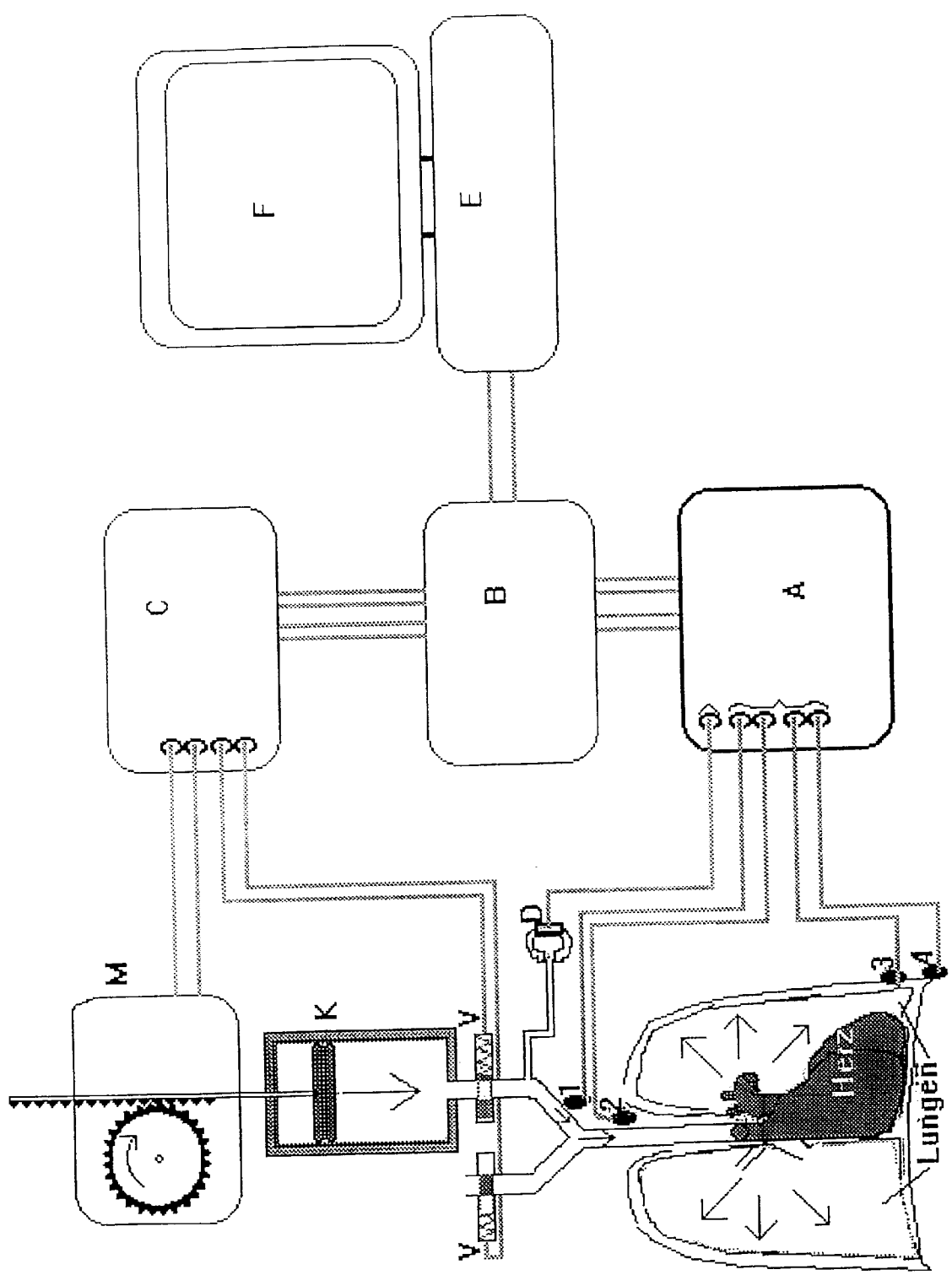
FIG. 1 is a schematic diagram showing a device and method of this invention.

An exemplary device (FIG. 1) carrying out the invention includes a device for the measurement of the impedance curves, which includes, at least two current electrodes, 1,4 connected to the chest or neck and connected to an alternating current generator of an impedance measuring device A and two measuring electrodes 2,3, which are connected to an amplifier of the impedance measuring device, or unit, A for measuring a body impedance between the current electrodes, as well as a pressure gauge device, D for the measurement of pressure inside the respirator system, which is connected to the impedance measuring device A.

The impedance measuring unit A is connected to a data processor unit B, for processing recorded impedance curves and respiration pressure curves, such as analysis of amplitudes, the minima and maxima, turning points, areas under the impedance curves, Zo, the velocity of impedance change dz/dt, the respiration pressure, and the velocity of respiration pressure changes.

The data processor unit B converts the impedance and pressure signals measured by the impedance amplifier A into steering impulses for engines and valves of the respirator.

Under assistance of a control unit E and a monitor F the processor can be informed in which way the signal measured by the impedance amplifier of the impedance measuring device A should be converted into steering impulses of the respirator engines and valves.

Additionally, all measured parameters can be stored and distributed by this control unit E. Curves measured by the impedance amplifier of the impedance measuring device A as well as other parameters, such as ventilation pressure can be depicted on the monitor F.

After amplification by a steering amplifier C, the engine M of the respirator pump K is directly driven by the impulses of the data processor unit B. Valves regulating the flow of breathing gas are driven by the output impulses of the data processor unit B after amplification by the steering amplifier too.

The impedance signal is measured and analyzed during each period of the respiration and cardiac cycles. For example, the cardiac output can be calculated and respiratory minute volume will be adapted to cardiac output under consideration of the measured oxygen and carbon dioxide concentrations in the system. That is, changes in the cardiac impedance output (impedance changes caused by changes in the size of the heart because of pump action) control the progress, or course, (Verlauf') or extent of movement of, or applications of, the respiratory gas and respiratory gas restore carried out by the respiratory apparatus.

The data processor unit B is informed by the steering amplifier C in which way the impedance curves should be converted into output pulses for the engine of the respirator. The output of the impulses by the processor can be freely defined and programmed by the steering unit.

As a simple example of the application of function, the respirator can be operated in such a way, that the insufflation of respiration air is performed during the diastolic interval of the heart cycle, whereas the respirator is stopped during the systolic ejection period of the ventricle.

In a further arrangement of the invention, the oxygen consumption or carbon dioxide enlargement can be measured within the device and these data might be used for the calibration of the values measured by the impedance measurement—for example the cardiac output—. It is also possible to use the measured values of oxygen and carbon dioxide to control the respirator.

What is claimed is:

1. Procedure of mechanical support of natural respiration and process of an artificial respiration with simultaneous registration of mechanical cardiac action via measurement of electric impedance variation within a region of the throat, breast and/or epigastrium, wherein a course of respiratory gas supply and respiratory gas restore carried out by respiratory apparatus is controlled by a course of a measured impedance curve which allows calculations of systolic discharge of a heart as well as heart minute volume which is, in turn, used to control the respiratory apparatus, whereby to measure the impedance curve:

a first current electrode is placed within a region of the right atrium through access via the vena cava or the esophagus or the trachea or another vessel in the mediastinum, and a second external current electrode is placed on the skin of the throat near the arteria carotis or the vena jugularis; and a first measuring electrode is placed within a region of right atrium through access via the vena cava or the esophagus or the trachea or another vessel of the mediastinum and a second external measuring electrode is placed on the skin of the throat within a region of the arteria carotis or vena jugularis, so that the measuring electrodes lie in the current path between the first and second current electrodes, whereby no lung tissue involved with the gas exchange is found on the traction of the measuring electrode.

2. Procedure of claim 1, wherein one or several electrical impedance- cardiograms with various alternating current frequencies and/or variously set placings of current and measuring electrodes to control respiration can be applied, whereby systolic discharge of the heart as well as heart minute volume can be calculated via evaluation of the impedance alteration curve and applied during control of the respiratory apparatus.

3. Procedure according to claim 1, wherein an influence of the impedance curves registered by the electric impedance measurement on the control of the respiration apparatus can be chosen freely and be changed, as well as a device for carrying out the procedure.

4. Procedure according claim 1, wherein the measured impedance that controls output of the respiration apparatus as well as a progress curve for respiration flow and respiration pressure are measured and recorded.

5. Procedure according to claim 1, wherein respiration concentration and respiration temperature are controlled by progress of the measured impedance curve.

6. Procedure according to claim 1, wherein progress of oxygen consumption in respiration or progress of an amount of exhaled carbon dioxide to calculate cardiac output are included with the impedance measurements.

7. Procedure according to claim 1, wherein progress of oxygen consumption in respiration or progress of an amount of exhaled carbon dioxide are used to control the respiration apparatus.

8. Procedure according to claim 1, wherein the external electrodes can be set in a ring shape around the throat and chest to be used as current or measuring electrodes.

9. Procedure of mechanical support of natural respiration and process of an artificial respiration with simultaneous registration of mechanical cardiac action via measurement of electric impedance variation within a region of the throat, breast and/or epigastrium, wherein a course of respiratory gas supply and respiratory gas restore carried out by respiratory apparatus is controlled by a course of a measured impedance curve, whereby to measure the impedance curve:

a first current electrode is placed within the region of the mediastinum through access via the vena cava or the esophagus or trachea or another vessel of the mediastinum and a second external current electrode is placed on the skin of the chest; and a first measuring electrode is placed within the region of the mediastinum through access via the vena cava or the esophagus or the trachea or another vessel of the mediastinum and a second external measuring electrode is placed on the skin of the chest, so that the measuring electrodes in the current path lie between the current electrodes, whereby lung tissue involved with the gas exchange was found on the traction between the measuring electrodes.

* * * * *